US009687671B2

(12) United States Patent
Weckwerth et al.

(10) Patent No.: US 9,687,671 B2
(45) Date of Patent: Jun. 27, 2017

(54) OPTICAL SENSOR AND METHOD FOR IDENTIFYING THE PRESENCE OF SKIN AND THE PIGMENTATION OF SKIN

(75) Inventors: Mark V. Weckwerth, Weckwerth, CA (US); Tobin C. Island, Oakland, CA (US); Robert E. Grove, Pleasanton, CA (US)

(73) Assignee: CHANNEL INVESTMENTS, LLC, Tampa, FL (US)

( * ) Notice: Subject to any disclaimer, the term of this patent is extended or adjusted under 35 U.S.C. 154(b) by 903 days.

(21) Appl. No.: 12/430,730

(22) Filed: Apr. 27, 2009

(65) Prior Publication Data

US 2009/0270848 A1 Oct. 29, 2009

Related U.S. Application Data

(60) Provisional application No. 61/048,154, filed on Apr. 25, 2008.

(51) Int. Cl.
*A61N 5/06* (2006.01)
*A61B 5/00* (2006.01)
*A61B 17/00* (2006.01)
*A61B 90/00* (2016.01)

(52) U.S. Cl.
CPC .......... *A61N 5/0616* (2013.01); *A61B 5/0059* (2013.01); *A61B 5/441* (2013.01); *A61B 5/6843* (2013.01); *A61B 2017/00057* (2013.01); *A61B 2090/065* (2016.02); *A61B 2562/0238* (2013.01); *A61N 2005/0652* (2013.01); *A61N 2005/0659* (2013.01); *A61N 2005/0662* (2013.01)

(58) Field of Classification Search
CPC ........ A61B 18/203; A61B 2018/00452; A61B 2018/00476; A61B 2017/00172; A61B 2017/00057; A61B 2018/00005; A61B 2018/2261; A61B 2090/065; A61B 2017/00061; A61B 2018/00029; A61B 18/20; A61B 2017/00066
See application file for complete search history.

(56) References Cited

U.S. PATENT DOCUMENTS

| | | | |
|---|---|---|---|
| 3,307,533 A | 3/1967 | Meredith et al. | 601/150 |
| 3,538,919 A | 11/1970 | Meyer | 606/36 |
| 3,622,743 A | 11/1971 | Muncheryan | 219/121.63 |
| 3,693,623 A | 9/1972 | Harte et al. | 606/9 |
| 3,821,510 A | 6/1974 | Muncheryan | 219/121.79 |
| 3,834,391 A | 9/1974 | Block | 128/303.1 |
| 4,140,130 A | 2/1979 | Storm, III | 607/154 |
| 4,232,678 A | 11/1980 | Skovajsa | 607/89 |
| 4,240,738 A | 12/1980 | Praamsma et al. | 355/1 |
| 4,354,092 A | 10/1982 | Manabe et al. | 219/225 |
| 4,388,924 A | 6/1983 | Weissman et al. | 606/9 |
| 4,423,736 A | 1/1984 | Dewitt et al. | 600/306 |
| 4,449,528 A | 5/1984 | Auth et al. | 606/31 |
| 4,551,628 A | 11/1985 | Grossman | 250/503.1 |
| 4,573,466 A | 3/1986 | Simada et al. | 606/11 |
| 4,592,353 A | 6/1986 | Daikuzono | 606/16 |
| 4,608,978 A | 9/1986 | Rohr | 606/9 |
| 4,617,926 A | 10/1986 | Sutton | 606/9 |
| 4,690,141 A | 9/1987 | Castel et al. | 607/90 |
| 4,733,660 A | 3/1988 | Itzkan | 606/9 |
| 4,829,262 A | 5/1989 | Furumoto | 359/346 |
| 4,846,184 A | 7/1989 | Comment et al. | 600/306 |
| 4,849,211 A | 7/1989 | Schrauzer | 424/45 |
| 4,860,744 A | 8/1989 | Johnson et al. | 128/303.1 |
| 4,905,690 A | 3/1990 | Ohshiro et al. | 607/89 |
| 4,930,504 A | 6/1990 | Diamantopoulos et al. | 607/88 |
| 5,057,104 A | 10/1991 | Chess | 606/9 |
| 5,059,013 A | 10/1991 | Jain | 359/503 |
| 5,059,192 A | 10/1991 | Zaias | 606/9 |
| 5,071,417 A | 12/1991 | Sinofsky | 606/8 |
| 5,075,971 A | 12/1991 | Mccambridge | 30/133 |

(Continued)

FOREIGN PATENT DOCUMENTS

| | | | | |
|---|---|---|---|---|
| CN | 2442726 Y | 8/2001 | | A63H 33/00 |
| DE | 19629978 A1 | 1/1998 | | F41A 33/02 |
| DE | 10044662 A1 | 3/2002 | | A61K 31/60 |
| DE | 10360503 A1 | 7/2005 | | A61K 8/06 |
| DK | WO2004/010884 A1 * | 2/2004 | | 606/9 |
| EP | 0761257 A2 | 3/1997 | | A61B 18/20 |
| EP | 0933096 A2 | 8/1999 | | A61B 17/00 |
| EP | 1116476 A2 | 7/2001 | | A61B 18/20 |
| EP | 1168535 A1 | 1/2002 | | H01S 5/022 |
| EP | 1358872 A1 | 11/2003 | | A61K 31/192 |
| FR | 2665366 A1 | 2/1992 | | A61N 1/32 |
| FR | 2932679 A1 | 12/2009 | | A61K 8/36 |

(Continued)

OTHER PUBLICATIONS

Brunsting, L.A. et al., "The Color of the Skin as Analyzed by Spectrophotometric Methods: II. The Role of Pigmentation," The Journal of Clinical Investigation, vol. 7, 18 pages, Apr. 29, 1929.

(Continued)

*Primary Examiner* — Audrea Buckley
(74) *Attorney, Agent, or Firm* — Slayden Grubert Beard PLLC (57) ABSTRACT

Apparatus and methods are provided to control a device, such as a light emitting dermatologic or cosmetic treatment device, and ensure that the device is in contact with skin while also determining the pigmentation level of skin. One or more light sources contact the skin and one or more detectors measure spectral remission from the skin. The obtained remission measurements are compared with known skin spectral remission values, and calibration allows measurements of absolute remission to be converted to fractional remission values. Skin pigmentation levels are compared to known base-line levels to determine and control appropriate treatment parameters. A temperature sensor allows correction for temperature variations. The apparatus may or may not be incorporated into the treatment device.

23 Claims, 4 Drawing Sheets

(56) References Cited

U.S. PATENT DOCUMENTS

| | | | |
|---|---|---|---|
| 5,107,832 A | 4/1992 | Guibert et al. ............... 607/96 |
| 5,109,465 A | 4/1992 | Klopotek .................... 385/133 |
| 5,226,907 A | 7/1993 | Tankovich .................. 606/133 |
| 5,233,337 A | 8/1993 | Takahashi ..................... 345/82 |
| 5,259,380 A | 11/1993 | Mendes et al. .............. 607/115 |
| 5,282,797 A | 2/1994 | Chess ............................ 606/9 |
| 5,295,052 A | 3/1994 | Chin et al. ................... 362/580 |
| 5,344,418 A | 9/1994 | Ghaffari .......................... 606/9 |
| 5,360,426 A | 11/1994 | Muller et al. ................. 606/13 |
| 5,401,270 A | 3/1995 | Muller et al. ................. 606/13 |
| 5,405,368 A | 4/1995 | Eckhouse ...................... 607/88 |
| 5,425,728 A | 6/1995 | Tankovich ...................... 606/9 |
| 5,431,647 A | 7/1995 | Purcell, Jr. et al. ........... 606/16 |
| 5,464,434 A | 11/1995 | Alt ................................. 607/6 |
| 5,464,436 A | 11/1995 | Smith ........................... 607/89 |
| 5,473,408 A | 12/1995 | Hoffman et al. ............... 355/53 |
| 5,481,385 A | 1/1996 | Zimmerman et al. ......... 349/62 |
| 5,486,172 A | 1/1996 | Chess .......................... 606/20 |
| 5,519,534 A | 5/1996 | Smith et al. ................. 359/599 |
| 5,549,660 A | 8/1996 | Mendes et al. ................ 607/88 |
| 5,556,612 A | 9/1996 | Anderson et al. ............. 424/59 |
| 5,578,022 A | 11/1996 | Scherson et al. ............ 604/304 |
| 5,595,568 A | 1/1997 | Anderson et al. ............... 606/9 |
| 5,606,798 A | 3/1997 | Kelman ........................ 30/41.5 |
| 5,611,798 A | 3/1997 | Eggers ........................... 606/31 |
| 5,624,435 A | 4/1997 | Furumoto et al. ............ 606/10 |
| 5,628,744 A | 5/1997 | Coleman et al. .............. 606/12 |
| 5,630,811 A | 5/1997 | Miller ............................. 606/9 |
| 5,632,741 A | 5/1997 | Zavislan et al. ................ 606/9 |
| 5,643,252 A | 7/1997 | Waner et al. ................... 606/9 |
| 5,647,866 A | 7/1997 | Zaiase et al. ................... 606/9 |
| 5,658,323 A | 8/1997 | Miller ........................... 607/89 |
| 5,662,643 A | 9/1997 | Kung, V et al. ................ 606/3 |
| 5,669,916 A | 9/1997 | Anderson .................... 606/133 |
| 5,683,380 A | 11/1997 | Eckhouse et al. .............. 606/9 |
| 5,700,240 A | 12/1997 | Barwick, Jr. et al. ........ 604/22 |
| 5,707,403 A | 1/1998 | Grove et al. .................. 607/89 |
| 5,728,090 A | 3/1998 | Martin et al. ................... 606/3 |
| 5,735,844 A | 4/1998 | Anderson et al. ............... 606/9 |
| 5,743,901 A | 4/1998 | Grove et al. .................... 606/9 |
| 5,752,948 A | 5/1998 | Tankovich et al. ............. 606/9 |
| 5,752,949 A | 5/1998 | Tankovich et al. ............. 606/9 |
| 5,766,214 A | 6/1998 | Mehl, Sr. et al. ............... 606/9 |
| 5,769,844 A | 6/1998 | Ghaffari ........................ 606/16 |
| 5,792,137 A | 8/1998 | Carr et al. ..................... 606/29 |
| 5,814,040 A | 9/1998 | Nelson et al. ................... 606/9 |
| 5,817,089 A | 10/1998 | Tankovich et al. ............. 606/9 |
| 5,820,625 A | 10/1998 | Izawa et al. .................... 606/9 |
| 5,824,023 A | 10/1998 | Anderson ...................... 607/88 |
| 5,830,208 A | 11/1998 | Muller ............................. 606/9 |
| 5,843,072 A | 12/1998 | Furumoto et al. .............. 606/9 |
| 5,846,252 A | 12/1998 | Mehl, Sr. ..................... 606/133 |
| 5,849,029 A | 12/1998 | Eckhouse et al. ........... 607/104 |
| 5,853,407 A | 12/1998 | Miller ............................. 606/9 |
| 5,868,732 A | 2/1999 | Waldman et al. ............... 606/9 |
| 5,871,479 A | 2/1999 | Furumoto et al. .............. 606/9 |
| 5,871,480 A | 2/1999 | Tankovich ....................... 606/9 |
| 5,871,521 A | 2/1999 | Kaneda et al. ................ 607/89 |
| 5,879,346 A | 3/1999 | Waldman et al. ............... 606/9 |
| 5,885,273 A | 3/1999 | Eckhouse et al. .............. 606/9 |
| 5,944,748 A | 8/1999 | Mager et al. .................. 607/88 |
| 5,966,210 A | 10/1999 | Rosow et al. ................ 356/213 |
| 5,968,034 A | 10/1999 | Fullmer et al. .................. 606/9 |
| 5,989,267 A | 11/1999 | Anderson .................... 606/133 |
| 6,015,404 A | 1/2000 | Altshuler et al. ................ 606/9 |
| RE36,634 E | 3/2000 | Ghaffari .......................... 606/9 |
| 6,059,765 A | 5/2000 | Cole et al. .................... 604/500 |
| 6,072,551 A | 6/2000 | Jannson et al. ................ 349/64 |
| 6,080,146 A | 6/2000 | Altshuler et al. ................ 606/9 |
| 6,096,029 A | 8/2000 | O'donnell, Jr. ................. 606/9 |
| 6,104,959 A | 8/2000 | Spertell ........................ 607/101 |
| 6,106,514 A | 8/2000 | O'donnell, Jr. ................. 606/9 |
| 6,114,862 A | 9/2000 | Tartagni et al. .............. 324/662 |
| 6,134,475 A | 10/2000 | Will .............................. 607/98 |
| 6,138,041 A | 10/2000 | Yahia ......................... 455/569.2 |
| 6,142,650 A | 11/2000 | Brown et al. ................. 365/259 |
| 6,144,536 A | 11/2000 | Zimmerman et al. ......... 361/31 |
| 6,160,831 A | 12/2000 | Kleinschmidt et al. ........ 372/57 |
| 6,168,831 B1 | 1/2001 | Khan et al. ................... 427/240 |
| 6,171,301 B1 | 1/2001 | Nelson et al. ................... 606/9 |
| 6,183,500 B1 | 2/2001 | Kohler .......................... 607/88 |
| 6,183,773 B1 | 2/2001 | Anderson .................... 424/450 |
| 6,188,495 B1 | 2/2001 | Inoue et al. .................. 398/139 |
| 6,197,020 B1 | 3/2001 | O'donnell, Jr. ................. 606/9 |
| 6,208,749 B1 | 3/2001 | Gutkowicz-Krusin et al. ............................ 382/128 |
| 6,214,034 B1 | 4/2001 | Azar .............................. 607/89 |
| 6,228,074 B1 | 5/2001 | Almeida ......................... 606/9 |
| 6,251,127 B1 | 6/2001 | Biel .............................. 607/88 |
| 6,264,649 B1 | 7/2001 | Whitcroft et al. ............. 606/22 |
| 6,269,818 B1 | 8/2001 | Lui et al. ...................... 128/898 |
| 6,273,884 B1 | 8/2001 | Altshuler et al. ................ 606/9 |
| 6,273,885 B1 | 8/2001 | Koop et al. ...................... 606/9 |
| 6,277,111 B1 | 8/2001 | Clement et al. ................. 606/9 |
| 6,280,438 B1 | 8/2001 | Eckhouse et al. .............. 606/9 |
| 6,290,713 B1 | 9/2001 | Russell ......................... 607/88 |
| 6,306,130 B1 | 10/2001 | Anderson et al. ............. 606/27 |
| 6,322,584 B2 | 11/2001 | Ingle et al. .................... 607/96 |
| 6,379,376 B1 | 4/2002 | Lubart ........................... 607/88 |
| 6,408,212 B1 | 6/2002 | Neev ........................... 607/100 |
| 6,413,255 B1 | 7/2002 | Stern ............................. 606/41 |
| 6,413,268 B1 | 7/2002 | Hartman ....................... 607/94 |
| 6,428,198 B1 | 8/2002 | Saccomanno et al. ........ 385/147 |
| 6,436,127 B1 | 8/2002 | Anderson et al. ............. 607/89 |
| 6,440,122 B1 | 8/2002 | Shimoji .......................... 606/2 |
| 6,441,943 B1 | 8/2002 | Roberts et al. ............... 359/267 |
| 6,451,007 B1 | 9/2002 | Koop et al. ...................... 606/9 |
| 6,485,484 B1 | 11/2002 | Connors et al. ................ 606/9 |
| 6,494,900 B1 | 12/2002 | Salansky et al. .............. 607/89 |
| 6,508,813 B1 | 1/2003 | Alshuler ......................... 606/9 |
| 6,511,475 B1 | 1/2003 | Altshuler et al. ................ 606/9 |
| 6,514,242 B1 | 2/2003 | Vasily et al. .................... 606/9 |
| 6,516,013 B1 | 2/2003 | Patzel et al. ................ 372/29.02 |
| 6,517,532 B1 | 2/2003 | Altshuler et al. ................ 606/9 |
| 6,533,775 B1 | 3/2003 | Rizoiu ............................ 606/9 |
| 6,536,914 B2 | 3/2003 | Hoelen et al. ................ 362/231 |
| 6,548,781 B1 | 4/2003 | Brunwinkel ............... 219/121.73 |
| 6,563,853 B2 | 5/2003 | Heist et al. ..................... 372/57 |
| 6,567,696 B2 | 5/2003 | Voznesensky et al. .......... 607/3 |
| 6,572,637 B1 | 6/2003 | Yamazaki et al. ............. 607/89 |
| 6,600,951 B1 | 7/2003 | Anderson ...................... 604/20 |
| 6,605,080 B1 | 8/2003 | Altshuler et al. ................ 606/3 |
| 6,610,052 B2 | 8/2003 | Furumoto ...................... 606/9 |
| 6,621,702 B2 | 9/2003 | Elias et al. .................... 361/700 |
| 6,637,924 B2 | 10/2003 | Pelka et al. ................... 362/555 |
| 6,641,044 B2 | 11/2003 | Plesko ...................... 235/462.49 |
| 6,648,904 B2 | 11/2003 | Altshuler et al. ............. 607/96 |
| 6,653,618 B2 | 11/2003 | Zenzie .......................... 250/221 |
| 6,659,999 B1 | 12/2003 | Anderson et al. ............... 606/9 |
| 6,660,000 B2 | 12/2003 | Neuberger et al. .............. 606/9 |
| 6,663,620 B2 | 12/2003 | Altshuler et al. ................ 606/9 |
| 6,663,659 B2 | 12/2003 | Mcdaniel ...................... 607/88 |
| 6,666,856 B2 | 12/2003 | Connors et al. ................ 606/9 |
| 6,723,090 B2 | 4/2004 | Altshuler et al. ................ 606/9 |
| 6,733,493 B2 | 5/2004 | Gruzdev et al. ................. 606/9 |
| 6,749,624 B2 | 6/2004 | Knowlton .................... 607/104 |
| 6,758,845 B1 | 7/2004 | Weckwerth et al. ............. 606/9 |
| 6,790,205 B1 | 9/2004 | Yamazaki et al. ............... 606/9 |
| 6,808,287 B2 | 10/2004 | Lebens et al. ................ 362/184 |
| 6,817,997 B2 | 11/2004 | Furuno et al. ................... 606/9 |
| 6,872,221 B2 | 3/2005 | Lytle ............................. 607/89 |
| 6,887,260 B2 | 5/2005 | Mcdaniel ...................... 607/88 |
| 6,902,563 B2 | 6/2005 | Wilkens et al. ................. 606/9 |
| 6,955,672 B2 | 10/2005 | Cense et al. .................... 606/9 |
| 6,957,905 B1 | 10/2005 | Pritchard et al. ............. 362/554 |
| 6,976,984 B2 * | 12/2005 | Cense et al. .................... 606/9 |
| 7,029,469 B2 | 4/2006 | Vasily ............................. 606/9 |
| 7,068,910 B2 | 6/2006 | Duine et al. .................. 385/146 |
| 7,077,544 B2 | 7/2006 | Parker .......................... 607/90 |
| 7,083,610 B1 | 8/2006 | Murray et al. .................. 606/9 |
| 7,115,123 B2 | 10/2006 | Knowlton et al. ............. 606/41 |
| 7,118,563 B2 | 10/2006 | Weckwerth et al. ............. 606/9 |
| 7,204,832 B2 | 4/2007 | Altshuler et al. ................ 606/9 |
| 7,250,045 B2 | 7/2007 | Island et al. ................... 606/17 |

(56) References Cited

U.S. PATENT DOCUMENTS

| | | | |
|---|---|---|---|
| 7,250,047 B2 | 7/2007 | Anderson et al. | 606/32 |
| 7,413,567 B2 | 8/2008 | Weckwerth et al. | 606/10 |
| 7,452,356 B2 | 11/2008 | Grove et al. | 606/9 |
| 7,762,964 B2 | 7/2010 | Slatkine | 601/7 |
| 7,981,111 B2 | 7/2011 | Grove et al. | 606/27 |
| 8,346,347 B2 | 1/2013 | Altshuler et al. | 600/476 |
| 8,551,104 B2 | 10/2013 | Weckwerth et al. | 606/89 |
| 8,709,003 B2 | 4/2014 | Island et al. | 606/9 |
| 2001/0023363 A1 | 9/2001 | Harth et al. | 607/90 |
| 2001/0046131 A1 | 11/2001 | Hoelen et al. | 362/231 |
| 2001/0048801 A1 | 12/2001 | Saccomanno et al. | 385/147 |
| 2002/0005475 A1 | 1/2002 | Zenzie | 250/221 |
| 2002/0015430 A1 | 2/2002 | Osmanow et al. | 372/55 |
| 2002/0031160 A1 | 3/2002 | Desor | 372/57 |
| 2002/0049483 A1 | 4/2002 | Knowlton | 607/101 |
| 2002/0091377 A1 | 7/2002 | Anderson et al. | 606/9 |
| 2002/0097587 A1 | 7/2002 | Krietzman et al. | 362/553 |
| 2002/0128635 A1 | 9/2002 | Altshuler et al. | 606/9 |
| 2002/0128695 A1 | 9/2002 | Harth et al. | 607/88 |
| 2002/0151887 A1 | 10/2002 | Stern et al. | 606/41 |
| 2002/0161357 A1 | 10/2002 | Anderson et al. | 606/9 |
| 2002/0161418 A1 | 10/2002 | Wilkens et al. | 607/90 |
| 2002/0173780 A1 | 11/2002 | Altshuler et al. | 606/9 |
| 2002/0173833 A1 | 11/2002 | Korman et al. | 607/88 |
| 2002/0183811 A1 | 12/2002 | Irwin | 607/94 |
| 2003/0004499 A1 | 1/2003 | Mcdaniel | 606/3 |
| 2003/0009158 A1 | 1/2003 | Perricone | 606/9 |
| 2003/0032950 A1 | 2/2003 | Altshuler et al. | 606/9 |
| 2003/0036751 A1 | 2/2003 | Anderson et al. | 606/9 |
| 2003/0046825 A1 | 3/2003 | Slingo | 34/96 |
| 2003/0050561 A1 | 3/2003 | Bazin et al. | 600/476 |
| 2003/0055413 A1 | 3/2003 | Altshuler et al. | 606/9 |
| 2003/0055414 A1 | 3/2003 | Altshuler et al. | 606/9 |
| 2003/0065314 A1 | 4/2003 | Altshuler et al. | 606/9 |
| 2003/0080755 A1 | 5/2003 | Kobayashi | |
| 2003/0094714 A1 | 5/2003 | Buazza et al. | 264/1.38 |
| 2003/0105069 A1 | 6/2003 | Robinson et al. | 514/185 |
| 2003/0112623 A1 | 6/2003 | Yu et al. | 362/118 |
| 2003/0133292 A1 | 7/2003 | Mueller et al. | 362/231 |
| 2003/0138249 A1 | 7/2003 | Merola et al. | 396/661 |
| 2003/0146122 A1 | 8/2003 | Westfield et al. | 206/349 |
| 2003/0169400 A1 | 9/2003 | Buazza et al. | 351/159.62 |
| 2003/0177657 A1 | 9/2003 | Andis et al. | 34/96 |
| 2003/0195494 A1 | 10/2003 | Altshuler et al. | 606/9 |
| 2003/0199859 A1 | 10/2003 | Altshuler et al. | 606/9 |
| 2003/0216795 A1 | 11/2003 | Harth et al. | 607/88 |
| 2003/0220633 A1 | 11/2003 | Angeley et al. | 606/18 |
| 2003/0232356 A1* | 12/2003 | Dooley et al. | 435/6 |
| 2003/0233138 A1 | 12/2003 | Spooner | 607/93 |
| 2004/0006328 A1 | 1/2004 | Anderson | 604/501 |
| 2004/0010298 A1 | 1/2004 | Altshuler et al. | 607/88 |
| 2004/0010299 A1 | 1/2004 | Tolkoff et al. | 607/88 |
| 2004/0034319 A1 | 2/2004 | Anderson et al. | 604/20 |
| 2004/0034341 A1 | 2/2004 | Altshuler et al. | 606/3 |
| 2004/0036975 A1 | 2/2004 | Slatkine | 359/584 |
| 2004/0046108 A1 | 3/2004 | Spector | 250/227.13 |
| 2004/0054386 A1 | 3/2004 | Martin et al. | 607/88 |
| 2004/0073079 A1 | 4/2004 | Altshuler et al. | 600/1 |
| 2004/0093042 A1 | 5/2004 | Altshuler et al. | 607/88 |
| 2004/0116913 A1 | 6/2004 | Pilcher et al. | 606/9 |
| 2004/0120151 A1 | 6/2004 | Ostler et al. | 362/294 |
| 2004/0122492 A1 | 6/2004 | Harth et al. | 607/88 |
| 2004/0147985 A1 | 7/2004 | Macfarland et al. | 607/90 |
| 2004/0167499 A1 | 8/2004 | Grove et al. | 606/9 |
| 2004/0167500 A1 | 8/2004 | Weckwerth et al. | 606/9 |
| 2004/0167501 A1 | 8/2004 | Island et al. | 606/9 |
| 2004/0167502 A1 | 8/2004 | Weckwerth et al. | 606/9 |
| 2004/0167592 A1 | 8/2004 | Grove et al. | 607/88 |
| 2004/0176754 A1 | 9/2004 | Island et al. | 606/9 |
| 2004/0176823 A1 | 9/2004 | Island et al. | 607/88 |
| 2004/0225339 A1 | 11/2004 | Yaroslavsky et al. | 607/88 |
| 2004/0233655 A1 | 11/2004 | Zimmerman et al. | 362/19 |
| 2004/0241254 A1 | 12/2004 | Kopas et al. | 424/727 |
| 2004/0252940 A1 | 12/2004 | Atac et al. | 385/31 |
| 2005/0008049 A1 | 1/2005 | Oomori et al. | 372/36 |
| 2005/0038418 A1 | 2/2005 | Altshuler et al. | 606/9 |
| 2005/0069566 A1 | 3/2005 | Tamarkin et al. | 424/401 |
| 2005/0085878 A1 | 4/2005 | Wilkens et al. | 607/94 |
| 2005/0107849 A1 | 5/2005 | Altshuler et al. | 607/88 |
| 2005/0186168 A1 | 8/2005 | Albin et al. | 424/70.14 |
| 2005/0234527 A1 | 10/2005 | Slatkine | 607/89 |
| 2005/0276072 A1 | 12/2005 | Hayashi et al. | 362/609 |
| 2006/0142750 A1 | 6/2006 | Da Silva et al. | 606/27 |
| 2006/0149343 A1 | 7/2006 | Altshuler et al. | 607/90 |
| 2006/0206103 A1 | 9/2006 | Altshuler et al. | 606/9 |
| 2007/0025947 A1 | 2/2007 | Hansenne et al. | 424/70.22 |
| 2007/0027440 A1 | 2/2007 | Altshuler et al. | 606/9 |
| 2007/0032847 A1* | 2/2007 | Weckwerth et al. | 607/93 |
| 2007/0038206 A1 | 2/2007 | Altshuler et al. | 606/20 |
| 2007/0042020 A1 | 2/2007 | Howard | 424/439 |
| 2007/0060819 A1* | 3/2007 | Altshuler et al. | 600/475 |
| 2007/0129711 A1 | 6/2007 | Altshuler et al. | |
| 2007/0198004 A1 | 8/2007 | Altshuler et al. | 606/9 |
| 2007/0248590 A1 | 10/2007 | Milne et al. | 424/130.1 |
| 2007/0292461 A1 | 12/2007 | Tamarkin et al. | 424/401 |
| 2007/0299244 A1 | 12/2007 | Chaki et al. | 530/303 |
| 2008/0027518 A1 | 1/2008 | Island et al. | 607/88 |
| 2008/0077198 A1 | 3/2008 | Webb et al. | 607/88 |
| 2008/0125834 A1 | 5/2008 | Hendrix et al. | 607/88 |
| 2008/0147053 A1 | 6/2008 | Kang et al. | 606/9 |
| 2009/0043294 A1 | 2/2009 | Island et al. | 606/9 |
| 2009/0270848 A1 | 10/2009 | Weckwerth et al. | 606/9 |
| 2010/0069898 A1 | 3/2010 | O'neil et al. | 606/9 |

FOREIGN PATENT DOCUMENTS

| | | | | |
|---|---|---|---|---|
| JP | 06-273758 A | 9/1994 | | G02F 1/1335 |
| JP | 06-334950 A | 12/1994 | | H04N 5/74 |
| JP | 11244295 A | 9/1999 | | A61B 18/20 |
| JP | 2000300683 A | 10/2000 | | A61B 18/20 |
| JP | 2000515410 | 11/2000 | | A61B 18/20 |
| JP | 2001252363 A | 9/2001 | | A61B 17/00 |
| JP | 2002253573 A | 9/2002 | | A61B 18/20 |
| JP | 2003024458 A | 1/2003 | | A61N 5/06 |
| JP | 2004136019 A | 5/2004 | | A45D 26/00 |
| JP | 2004527330 A | 9/2004 | | A61B 17/00 |
| JP | 2004533866 A | 11/2004 | | A61B 18/18 |
| JP | 2005278724 A | 10/2005 | | A45D 26/00 |
| JP | 2006192073 A | 7/2006 | | A61N 5/06 |
| JP | 2006518614 A | 8/2006 | | A61B 18/20 |
| JP | 2006525036 A | 11/2006 | | A61B 17/00 |
| JP | 2007508243 A | 4/2007 | | A61K 31/025 |
| JP | 2009509140 A | 3/2009 | | A61B 5/00 |
| JP | 5146517 B2 | 2/2013 | | H01L 21/28 |
| WO | 96/14083 A1 | 5/1996 | | A23L 1/015 |
| WO | 00/02491 A1 | 1/2000 | | A61K 41/00 |
| WO | 02/094116 A1 | 11/2002 | | A61B 18/18 |
| WO | 03/001984 A2 | 1/2003 | | |
| WO | 03/017824 A2 | 3/2003 | | A61B 18/00 |
| WO | 03/043697 | 5/2003 | | A61N 5/06 |
| WO | 03/049633 A1 | 6/2003 | | A45D 26/00 |
| WO | 2004/075731 A2 | 9/2004 | | A61B 18/20 |
| WO | 2004/080279 A2 | 9/2004 | | A61B 18/20 |
| WO | 2005/063193 A1 | 7/2005 | | A61K 8/06 |
| WO | 2007/019536 A2 | 2/2007 | | A61B 18/20 |
| WO | 2009/089177 A1 | 7/2009 | | A61N 1/00 |

OTHER PUBLICATIONS

Brunsting, L.A. et al., "The Color of the Skin as Analyzed by Spectrophotometric Methods: III. The Role of Superficial Blood," The Journal of Clinical Investigation, vol. 7, 21 pages, Apr. 29, 1929.

Brown, E.B., "Modern Optics," Radiometry and Photometry, Reinhold Publishing Corporation, 3 pages, 1965.

Cornelius, C.E. et al., "Red Fluorescence of Comedones: Production of Porphyrins by Corynebacterium Acnes," The Journal of Investigative Dermatology, vol. 49(4), PMID: 4228644, [PubMed—Indexed for Medline], 3 pages, Oct. 1967.

Formanek, I. et al., "Porphyrinsynthesis by Propionibacterium Acnes (author's translation)," Archives for Dermatological (56) References Cited

OTHER PUBLICATIONS

Research, vol. 259(2), German, PMID: 334087 [PubMed—indexed for Medline], 9 pages, Aug. 22, 1977.
Lee, W.L. et al., "Comparative Studies of Porphyrin Production in Propionibacterium Acnes and Propionibaceterium Granulosum," Journal of Bacteriology, vol. 133(2), PMID: 637914 [PubMed—Indexed for Medline] 5 pages, Aug. 25, 1977.
Mills, O.H. et al., "Ultraviolet Phototherapy and Photochemotherapy of Acne Vulgaris," Archives of Dermatological Research, vol. 114(2), PMID: 147054 [PubMed: Indexed for Medline] 3 pages, Feb. 1978.
Fanta, D. et al., "Porphyrinsynthesis of Propionibacterium Acnes in Acne and Seborrhea (author's translation)," Archives of Dermatological Research, vol. 261, German, PMID: 148872 [PubMed—indexed for Medline], 5 pages, Apr. 7, 1978.
McGinley, K.J. et al., "Facial Follicular Porphyrin Fluorescence: Correlation with Age and Density of Propionibacterium Acnes," British Journal of Dermatology, Vo. 102(4), PMID: 7387886 [PubMed—Indexed for Medline] 5 pages, Jul. 24, 1979.
Sliney, D. et al., "Safety with Lasers and Other Optical Sources, a Comprehensive Handbook," Plenum Press, 9 pages, Jul. 1980.
Fanta, D. et al., "Porphyrin Synthesis by Propionibacteria in Dependence of External Factors," Archives of Dermatological Research, vol. 271, 7 pages, Jul. 10, 1980.
Melo, T.B. et al., "In Vivo Porphyrin Fluorescence for Propionibacterium Acnes. A Characterization fo the Fluorescing Pigments," Dermatologica, vol. 164(3), PMID: 7084539 [PubMed—Indexed for Medline] 9 pages, Mar. 1982.
Parrish, J. et al., "Erythema and Melanogenesis Action Spectra of Normal Human Skin," Photochemistry and Photobiology, vol. 36, 5 pages, Mar. 15, 1982.
Kjeldstad, B. et al., "Influence of pH on Porphyrin Production in Propionibacterium Acnes," Archives of Dermatological Research, vol. 276(6), PMID: 6517611 [PubMed—Indexed for Medline] 5 pages, 1984.
Melo, T.B. et al., "Photodestruction of Propionibacterium Acnes Porphyrins," Z. Naturforsch, vol. 40(C), PMID: 3993179 [PubMed—Indexed for Medline] 4 pages, Oct. 22, 1984.
Kjeldstad, B. et al., "Porphyrin Photosensitization of Bacteria," Adv. Exp. Med. Biol., PMID: 4096295 [PubMed—indexed for Medline], 5 pages, 1985.
Kjeldstad, B. et al., "An Action Spectrum for Blue and Near Ultraviolet Inactivation of Propionibacterium Acnes; with Emphasis on a Possible Porphyrin Photosensitization," Photochemistry and Photobiology, vol. 43(1), PMID: 3952162 [PubMed—Indexed for Medline] 4 pages, Jul. 19, 1985.
Guideline for Limits of Exposure to Ultraviolet Radiation of Wavelengths between 180 nm and 400 nm, Health Physics, vol. 49, No. 2, 10 pages, Aug. 1985.
Meffert, H. et al., "Phototherapy of Acne Vulgaris with the "TuR" UV 10 Body Section Irradiation Unit [translation]," Dermatol. Monatsscher., vol. 172, German, PMID: 2938991 [PubMed—Indexed for Medline] 6 pages, 1986.
Meffert, H. et al., "Phototherapy of Acne Vulgaris with the UVA Irradiation Instrument TBG 400 [translation]," Dermatol. Monatsscher, vol. 172, German, PMID: 2937663 [PubMed—Indexed for Medline] 2 pages, 1986.
Johnsson, A. et al., "Fluorescence from Pilosebaceous Follicles," Archives of Dermatological Research, vol. 279(3), PMID: 3592747 [PubMed—Indexed for Medline] 4 pages, 1987.
Meffert, H. et al., "Treatment of Acne Vulgaris with Visible Light [translation]," Dermatol. Monatsscher, vol. 173, German, PMID: 2963772 [PubMed—Indexed for Medline] 2 pages, 1987.
Meffert, H. et al., "Therapy of Acne with Visible Light. Decreased Irradiation Time by Using a Blue-Light High-Energy Lamp [translation]" Dermatol. Monatsschr., German, PMID: 2150382 [PubMed—Indexed for Medline] 7 pages, 1990.
Kjeldstad, B. et al., "Near-UV-Induced Radicals in Propionibacterium Acnes, Studied by Electron Spin Resonance Spectrometry at 77 K.," Journal of Photochemistry and Photobiology, vol. 9(2), PMID: 1650821 [PubMed—Indexed for Medline] 7 pages, Sep. 21, 1990.
Morys et al., "The Accurate Measurements of Biologically Effective Ultraviolet Radiation," International Symposium on High Latitude Optics, 10 pages, Jul. 1993.
Webster, G.F., "Inflammation in Acne Vulgaris," Journal of the American Academy of Dermatology, vol. 33(2 Pt. 1), Review, PMID: 7622652 [PubMed—Indexed for Medline] 7 pages, Aug. 1995.
Leung, S., "The Porphyrin Page," website at http://www.washburn.edu-cas-chemistry-sleung-porphyrin/page.html, Created Apr. 16, 1996, Last Modified Nov. 11, 2002, printed Jun. 22, 2004, 7 pages, Apr. 16, 1996.
Arakane, K. et al., "Singlet Oxygen (1 delta g) Generation from Coproporphyrin in Propionibacterium Acnes on Irradiation," Biochemical and Biophysical Research Communication, vol. 223, Article No. 0937, PMID: 8687438 [PubMed—Indexed for Medline], 6 pages, Jun. 25, 1996.
Sigurdsson, V. et al., "Phototherapy of Acne Vulgaris with Visible Light," Dermatology, vol. 194(3), PMID: 9187844 [PubMed—Indexed for Medline] 5 pages, Nov. 15, 1996.
Predicate Devices: LightSheer Diode Laser System by Star Medical/Coherent Star, K973324, K982940, K001746, 1997.
Leydon, J., "Therapy for Acne Vulgaris," The New England Journal of Medicine, Review Article, 6 pages, Apr. 17, 1997.
UV Index definition, Canadian Environmental Web page, See entire document, 3 pages, Jun. 1, 1998.
Code of Federal Regulations, Class I Accessible Emmission Limits for Laser Radiation, Food and Drug Administration, HHS, 2 pages, Apr. 1, 1999.
IEC Technical Report 60825-8, "Safety of Laser Products—Guide for the Safe Use of Medical Laser Equipment," 6 pages, Nov. 1999.
Papageorgiou, P. et al., "Phototherapy wit Blue (415 nm) and Red (660 nm) Light in the Treatment of Acne Vulgaris," British Journal of Dermatology, vol. 142(5), PMID: 10809858 [PubMed—indexed for Medline] 6 pages, Dec. 7, 1999.
Angelopoulou, E. et al., "The Reflectance Spectrum of Human Skin," Technical Report, Department of Computer and Information Science, 15 pages, Dec. 20, 1999.
Romiti, R. et al., "High-Performance Liquid Chromatography Analysis of Porphyrins in Propionibacterium Acnes," Archives of Dermatological Research, vol. 292(6), PMID: 10929774 [PubMed—Indexed for Medline] 3 pages, Jan. 7, 2000.
Shalita, A. et al., "Acne Photoclearing (APC) Using a Novel, High-Intensity, Enhanced, Narrow-Band, Blue Light Source," Clinical Application Notes, vol. 9(1), ESC Medical Systems Ltd., PB 558-0230, Rev. A, 4 pages, 2001.
International Standard IEC 60825.1, Safety of Laser Products—Part 1: Equipment Classification, Requirements and User's Guide, Editon 1.2, 121 pages, 2001.
Kawada, A. et al., "Acne Phototherapy with a High-Intensity, Enhanced, Narrow-Band, Blue Light Source: An Open Study and In Vitro Investigation," Journal of Dermatological Science, vol. 30(2), PMID: 12413768 [PubMed—indexed for Medline] 7 pages, Jun. 19, 2002.
Ashkenazi, H. et al., "Eradication of Propionibacterium Acnes by its Endogenic Porphyrins after Illumination with High Intensity Blue Light," FEMS Immunology and Medical Microbiology, vol. 35(1), PMID: 12589953 [PubMed: Indexed for MedLine], 8 pages, Jul. 24, 2002.
Harnessing Light to Treat Stretch Marks and Other Hypopigmented Scars, Skin & Aging, Supplement to Nov. 2002 Skin & Aging.
Hode, L., "Are Lasers More Dangerous than IPL Instruments?," Lasers in Surgery and Medicine, Supplement 15, 3 pages, 2003.
U.S. Appl. No. 60/450,243, by Robert E. Grove, entitled "Method and Apparatus for the Treatment of Benign Pigmented Lesions", filed Feb. 25, 2003.
U.S. Appl. No. 60/450,598, by Robert E. Grove, entitled "Personal Light Based Acne Treatment Device and Method", filed Feb. 26, 2003.

(56) References Cited

OTHER PUBLICATIONS

U.S. Appl. No. 60/451,091, by Robert E. Grove, entitled "Method and Device for Handheld and Cordless Light-Based Epilation", filed Feb. 28, 2003.
U.S. Appl. No. 10/794,676, by Mark V. Weckworth et al. entitled "Method and Apparatus for the Repigmentation of Human Skin", filed Mar. 3, 2004.
U.S. Appl. No. 60/452,304, by Robert E. Grove, entitled "Optical Sensor and Method for Identifying the Presence of Skin", filed Mar. 4, 2003.
U.S. Appl. No. 60/451,981, by Robert E. Grove, entitled "Method and Apparatus for the Repigmentation of Human Skin", filed Mar. 4, 2003.
U.S. Appl. No. 60/452,591, by Robert E. Grove, entitled "Method and Device for Sensing Skin Contact", filed Mar. 6, 2003.
U.S. Appl. No. 60/456,379, by Robert E. Grove, entitled "Apparatus and Method for the Radiative Treatment of Skin with Increased Eye Safety", filed Mar. 20, 2003.
U.S. Appl. No. 60/456,586, by Robert E. Grove, entitled "Handheld Dermatological Treatment Device with Power Meter", filed Mar. 21, 2003.
U.S. Appl. No. 60/458,861, by Robert E. Grove, entitled "Method and Apparatus for Dermatologic Treatment Utilizing Battery-Powered Laser Diode Bars", filed Mar. 27, 2003.
U.S. Appl. No. 60/472,056, by Robert E. Grove, entitled "Apparatus and Method for Dermatologic Treatment", filed May 20, 2003.
Micro Touch Trimmer website, www.asseenontvwork.com/vcc/ideavillage/microtouch/104917, printed Dec. 4, 2003, 21 pages.
EP Office Action, Application No. 04 714 604.8, 5 pages, Nov. 16, 2010.
EP Office Action, Application No. 04 714 910.1, 6 pages, Nov. 16, 2010.
Supplemental EP Search Report, Application No. 04 712 911.9, 3 pages, Dec. 6, 2010.
Supplemental EP Search Report, Application No. 04 712 922.6, 3 pages, Dec. 7, 2010.
Shnitkind, E. et al., "Anti-Inflammatory Properties of Narrow Band Blue Light," Poster Presentation (Conference Unknown), 1 page.
Predicate Devices: SLP 1000 (LC 100) Diode Laser of Palomar Medical Technologies, K010580, K011747.
Predicate Devices: Apex 800 Pulsed Diode Laser of Iridex Corporation, K020849.
Predicate Devices: F1 Pulsed Diode Laser of Opus Medical, Inc., K030235.
Predicate Devices: LightSheer Diode Laser System manufactured by Lumenis, Ltd.
Predicate Devices: Quantum Flash Lamp System Manufactured by Lumenis, Ltd.
Predicate Devices: CoolGlide Excel YAG Laser by Altus, Inc.
Predicate Devices: Devices by Ya-Man Ltd., of Tokyo, Japan.
Predicate Devices: Oriel Instruments Model 48010, by Spectra-Physics, Stratford, CT.
Predicate Devices: Panasonic part No. P-170SCW, or HHR300SCP Ni-MH Rechargables, Panasonic P-170SCRP NiCd, by Panasonic Matsushita Electric Corporation of America, Secaucus, NJ.
Predicate Devices: Laser Diode Bar Packages, Part No. ASM06C040W08010B80, Cutting Edge Optronics, of St. Charles, MO.
Predicate Devices: Part No. HX8-101 or FAN-101, or CP 0.8-31-06L, from Melcor.
Predicate Devices: PIC18LF452, manufactured by Microchip Technologies of Chandler, AZ.
Predicate Devices: Transistors IRL3716 (International Rectifier Corp., El Segundo, CA).
Palomar Super Long Pulse Diode Laser System, Clinical Data, Palomar Medical Technologies brochure.
Japanese Office Action, Application No. 2011-527040, 14 pages, Feb. 21, 2014.
Miller, Steve et al., "Isolation and Characterization of Protoporphyrin IX from Bacterial Catalase," The Journal of Biological Chemistry, vol. 235, No. 11, 3 pages, Mar. 7, 1960.
Dalton, J. et al., "Reaction Between Molecular Oxygen and Photoexcited Protoporphyrin IX," Nature, vol. 235, 1 pages, Feb. 18, 1972.
Hoeffler, Ulrich, "Enzymatic and Hemolytic Properties of Propionibacterium Acnes and Related Bacteria," Journal of Clinical Microbiology, vol. 6, No. 6, 4 pages, Jun. 10, 1977.
Diffey, B. L. "The consistency of studies of ultraviolet erythema in normal human skin." Physics in medicine and biology 27.5, 6 pages, 1982.
Meffert, H. et al., "Verkuzung der Bestrahlungszeit Verwendung eines Hochruckstrahlers vom Blaulichttyp," Dermatol. Mon. schr 176, 8 pages, 1990.
Karu, Tiina, "Primary and Secondary Mechanisms of Action of Visible to Near-IR Radiation on Cells," Journal of Photochemistry and Photobiology, vol. 49, 17 pages, Nov. 9, 1998.
Saiki, Hiroyasu et al., "Diffusion of Porphyrins and Quinones in Organic Solvents," Phys. Chem. Chem Phys., vol. 1, 4 pages, 1999.
Yoo, Yeong-Min et al., "Hemoglobin Toxicity in Experimental Bacterial Peritonitis Is Due to Production of Reactive Oxygen Species," Clinical and Diagnostic Laboratory Immunology, vol. 6, No. 6, 2 pages, Jul. 12, 1999.
Bagdonas, Saulius et al., "Phototransformations of 5-Aminolcvulinic Acid-Induced Protoporphyrin IX in Vitro: A Spectroscopic Study," Photochemistry and Photobiology, vol. 72(2), 7 pages, May 6, 2000.
Koval'skaya, N.E. et al., "The Efficiency of the Formation of Singlet Oxygen by a Sensitizer Based on Zinc Phthlocyanine," Journal of Applied Spectroscopy, vol. 68, No. 2, 4 pages, 2001.
Buchczyk, Darius P. et al., "High Efficiency of 5-Aminolevulinate-Photodynamic Treatment Using UVA Irradiation," Carcinogenesis, vol. 22, No. 6, 5 pages, 2001.
Mason, Maria G. et al., "Extracellular Heme Peroxidases in Actinomycetes: a Case of Mistaken Identity," Applied and Environmental Microbiology, vol. 67, No. 10, 8 pages, Jul. 18, 2001.
Jappe, U. et al., "Propionibacterium Acnes and Inflammation in Acne; P. Acnes has T-Cell Mitogenic Activity," British Journal of Dermatology, vol. 146, 8 pages, Sep. 12, 2001.
Elman et al., "The Effective Treatment of Acne Vulgaris by a High-Intensity, Narrow Band 405-420 nm Light Source," Journal of Cosmetic & Laser Therapy, vol. 5, 6 pages, Nov. 27, 2002.
Wagener, Frank et al., "Different Faces of the Heme-Heme Oxygenase System in Inflammation," Pharmaceutical Reviews, vol. 55, No. 3, The American Society for Pharmacology and Experimental Therapeutics, 21 pages, 2003.
Anonymous, "Akne-Guidelines Schweiz," [Online], Martin Pletscher: Dermatologie, Retrieved from Internet: http://www.martinpletscher.ch/dermatologie/akne.html, 5 pages, May 15, 2003.
Burkhart, Craig N. et al., "Assessment of Etiologic Agents in Acne Pathogenesis," Review, Department of Microbiology and Immunology, and Dermatology, Medical College of Ohio at Toledo, 7 pages, Jul. 2003.
Charakida, A. et al., "Phototherapy in the Treatment of Acne Vulgaris," American Journal of Clinical Dermatology, vol. 5(4), Adis. Data Information, 6 pages, 2004.
Elman, M. et al., "Light Therapy in the Treatment of Acne Vulgaris," Dermatological Surgery, vol. 30(2), Dermatology and Lasers Clinic, Tel Aviv and Caesarea, Israel, American Society for Dermatology Surgery, 8 pages, Feb. 2004.
Elman, M. et al., "The Role of Pulsed Light and Hear Energy (LHE) in Acne Clearance," Journal of Cosmetic Laser Therapy, vol. 6, 5 pages, Apr. 1, 2004.
Omi, Tokuya et al., "420 nm Intense Continuous Light Therapy for Acne," Journal of Cosmetic Laser Therapy, vol. 6, 7 pages, Aug. 12, 2004.
Krautheim, A. et al., "Acne: Topical Treatment," Clinics in Dermatology, vol. 22, No. 5, XP004647111, 10 pages, Sep. 1, 2004.
Ross, Victor E., "Optical Treatment for Acne," Dermatologic Therapy, vol. 18, ISSN 1396-0296, 14 pages, 2005.
Ross, Victor E., "Acne, Lasers, and Light," Advances in Dermatology, vol. 21, 29 pages, 2005.

(56) References Cited

OTHER PUBLICATIONS

Ortiz, Arisa et al., "A Review of Lasers and Light Sources in the Treatment of Acne Vulgaris," Journal of Cosmetic and Laser Therapy, vol. 7, 7 pages, Mar. 7, 2005.
Hamblin, M. et al., "Helicobacter Phylori Accumulates Photoactive Porphyrins and Is Killed by Visible Light," Antimicrobial Agents and Chemotherapy, vol. 49, No. 7, American Society for Microbiology, 6 pages, Mar. 7, 2005.
Mariwalla, Kavita et al., "Use of Lasers and Light-Based Therapies for Treatment of Acne Vulgaris," Lasers in Surgery and Medicine, vol. 37, 10 pages, Oct. 12, 2005.
Mariwalla, Kavita et al., "Non-Traditional Acne Therapy: The Use of Lasers and Light-Based Therapies," US Dermatology Review 2006, 4 pages, 2006.
Tremblay, J.F. et al., "Light-Emitting Diode 415 nm in the Treatment of Inflammatory Acne: An Open-Label, Multicentric, Pilot Investigation," Journal of Cosmetic and Laser Therapy, vol. 8, 3 pages, Jan. 25, 2006.
Goldberg, David J. et al., "Combination Blue (415 nm) and red (633 nm) LED Phototherapy in the Treatment of Mild to Severe Acne Vulgaris," Jornal of Cosmetic and Laser Therapy, vol. 8, 5 pages, Mar. 29, 2006.
Lee, Seung Yoon et al., "Blue and Red Light Combination LED Phototherapy for Acne Vulgaris in Patients with Skin Phototype IV," Lasers in Surgery and Medicine, vol. 39, 9 pages, Nov. 16, 2006.
Nestor, M., "The Use of Photodynamic Therapy for Treatment of Acne Vulgaris," Dermatologic Clinics, vol. 25, 11 pages, 2007.
"Light Dose Ranging Study of Photodynamic Therapy (PDT) with Levulan + Blue Light in Severe Facial Acne," DUSA Pharmaceuticals, Inc., http://clinicaltrials.gov/ct2/show/NCT00706433, 25 pages, Mar. 2007.
Anonymous, "BlueLight Acne Treatments," [Online], Retrieved from Internet: litttp://www.topdocs.com/display_procedure.php?id—bluelight, 2 pages, Apr. 10, 2008.
"Comparison of Claro to Other Dermatological Devices for Acne Treatment," Quantitative Assessment of Light Illumination on Organism Reduction; Subculture agar: TSA + 5% Sheep's Blood (Blood agar) Organism Diluent: Butterfield's Buffer or 0.85% Saline; Propionibacterium Acnes (ATCC 11827), 16 pages, Jun. 23, 2008.
Anonymous, "Vi Derm Product Line," [Online], Kalil Medical Products, Retrieved from Internet: http://www.kalilmedical.com/doctor/vi_derm_products.asp, 4 pages, Mar. 2, 2010.
International Search Report, Application No. PCT/US2009/056961, 7 pages, Jun. 29, 2010.
International Preliminary Report on Patentability, PCT/US2009/056961, 11 pages, Mar. 22, 2011.
International Preliminary Report on Patentability, PCT/US2009/057204, 8 pages, Mar. 22, 2011.
Supplementary European Search Report, Application No. 09815144, 9 pages, Feb. 10, 2012.
European Office Action, Application No. 09815144.2, 6 pages, Oct. 10, 2012.
European Search Report, Application No. 08797565.2, 6 pages, Oct. 29, 2012.
Japanese Office Action, Application No. 2010-520342, 6 pages, Mar. 7, 2013.
European Office Action, Application No. 09815144.2, 5 pages, Apr. 3, 2013.
Japanese Office Action, Application No. 2009-261364, 7 pages, Jun. 18, 2013.
Extended European Search Report, Application No. 13159309.7, 7 pages, May 7, 2013.
Japanese Office Action, Applcation No. 2011-506499, 5 pages, Nov. 26, 2013.
U.S Non-Final Office Action, U.S. Appl. No. 14/047,998, 7 pages, Jul. 5, 2016.
Balentine, Douglas A. et al., "The Chemistry of Tea Flavonoids," Critical Reviews in Food Science and Nutrition, vol. 37, No. 8, pp. 693-704 (12 pages total), 1997.
Dufresne, Christiane et al., "A Review of Latest Research Findings on the Health Promotion Properties of Tea," Journal of Nutritional Biochemistry, vol. 12, pp. 404-421 (18 pages total), 2001.
Non-Final Office Action, U.S. Appl. No. 14/047,998, 35 pages, Feb. 11, 2016.
U.S. Non-Final Office Action, U.S. Appl. No. 14/171,592, 39 pages, Nov. 23, 2016.
U.S. Final Office Action, U.S. Appl. No. 14/047,998, 6 pages, Jan. 6, 2017.
European Office Action, Application No. 13159309.7, 4 pages, May 8, 2014.
European Search Report, Application No. 09735456.7, 10 pages, Sep. 12, 2014.

\* cited by examiner

OPTICAL SENSOR AND METHOD FOR IDENTIFYING THE PRESENCE OF SKIN AND THE PIGMENTATION OF SKIN

RELATED APPLICATIONS

This application claims the benefit of U.S. Provisional Patent Application No. 61/048,154, filed Apr. 25, 2008, which is incorporated herein by reference. In addition, U.S. patent application Ser. No. 10/787,720, filed Feb. 25, 2004, now U.S. Pat. No. 7,413,567, issued on Aug. 19, 2008, U.S. Provisional Patent Application No. 60/450,243, filed Feb. 25, 2003; U.S. Provisional Patent Application No. 60/450, 598, filed Feb. 26, 2003; U.S. Provisional Patent Application No. 60/451,091, filed Feb. 28, 2003; U.S. Provisional Patent Application No. 60/452,304, filed Mar. 4, 2003, U.S. Provisional Patent Application No. 60/451,981 filed Mar. 4, 2003; U.S. Provisional Patent Application No. 60/452,591, filed Mar. 6, 2003; U.S. Provisional Patent Applications No. 60/456,379, filed Mar. 20, 2003; U.S. Provisional Patent Application No. 60/456,586, filed Mar. 21, 2003; U.S. Provisional Patent Applications No. 60/458,861 filed Mar. 27, 2003, U.S. Provisional Patent Application No. 60/472, 056, filed May 20, 2003, and U.S. Provisional Patent Application No. 61/048,154, filed Apr. 25, 2008, are also incorporated herein by reference.

FIELD OF THE INVENTION

The present application relates generally to devices and methods for differentiating human skin from other materials, and more particularly relates to devices and methods for optically differentiating human skin on a live person from other materials including other human tissue.

BACKGROUND OF THE INVENTION

Prior art devices that attempt to optically detect human skin have typically suffered from a number of limitations. Among them have been the issues of temperature sensitivity, that is, performance fluctuations caused by variations in operating or environmental temperature; variations in output power of the source, or sensitivity of the sensor.

Firstly, the device as described may be sensitive to temperature fluctuations. Since the LED's used as optical sources have an optical output power that depends on the temperature of the LED, the precise output power of each of the LED sources may vary with ambient temperature and may vary due to self-heating or by heating from the control electronics. Additionally, since the sensitivity of the phototransistor used to detect the remitted light may depend on the temperature of the phototransistor, the measurement of the remitted light may vary due to self-heating or by heating from the control electronics. Sources that vary in output power will affect the amount of light remitted. A phototransistor which has a sensitivity to temperature will give a measurement that has some error in the actual amount of remitted light.

Further, skin sensors in the prior art typically indicate only a broad indication of the presence of skin, which is less than ideal in at least some instances. None of the prior art measures the actual spectral remission at multiple wavelengths and reports that spectral remission for each wavelength as the fractional amount of light remitted at each wavelength. Thus, in the present invention, the ratio of the amount of light remitted at each wavelength is divided by the amount of light of that wavelength incident on the skin, and this fraction is then available for further use.

In addition, the prior art is typically unable to ascertain the degree of pigmentation of the skin. This is desirable in at least some applications, especially for devices which rely upon thermolysis.

As a result, there are significant shortcomings with prior art devices, and there has been a long felt need for a device and a technique which overcomes or substantially reduces these limitations.

SUMMARY OF THE INVENTION

In accordance with the present invention, a single broad-band source, or alternatively, multiple sources each of a unique emission spectra are used to illuminate a surface of interest. Multiple detectors each sensitive to a unique optical band or, alternatively, a single broad-band detector, respectively, is used to measure the amount of light remitted from said surface in each of the unique optical bands. Thus, a single broadband source can be used with multiple detectors each sensitive to a narrow wavelength band, or, alternatively, multiple narrow band sources with a single broadband detector. Still further, if increased cost and complexity is acceptable, multiple narrow band sources can be used with multiple narrow band detectors. In such a way, the spectral remission of the surface can be measured.

The spectral remission of skin, and particularly human skin in at least some embodiments, is characteristically different from most other materials. Therefore by obtaining the spectral remission from a surface of interest and by then comparing the obtained spectral remission to the spectral remission that is known to be skin one can determine whether the surface of interest is skin.

The present invention also addresses various other shortcomings of the prior art. While typical prior art optical skin-sensing devices can give variable results depending upon the operating temperature of the device, the present invention overcomes this limitation.

Therefore, the present invention provides a method for calibrating the skin sensor so that measurements of absolute remission can be converted to fractional remission.

In another embodiment of the present invention, a sensor is provided that can determine the presence of skin and also the pigmentation level of the skin.

The present invention further provides a device that is much less sensitive to ambient temperature conditions and is less sensitive to temperature variations caused by self-heating within the device.

In a preferred embodiment of the present invention a dermatological treatment device is provided which is self-contained, hand-held, and battery powered, and which has a skin sensor that compensates for temperature fluctuations and inhibits the emission of the treatment device unless the presence of skin is detected. In this preferred embodiment the sensor further detects the pigmentation level of the skin and emission of the treatment device is inhibited unless the pigmentation level of the skin is less than a predetermined level.

Alternatively, for some embodiments, the emission of the treatment device can be adjusted in accordance with the pigmentation level of the skin.

These and other attributes of the present invention may be better appreciated from the following description of the invention, together with the Figures.

DETAILED DESCRIPTION OF THE PREFERRED EMBODIMENTS

Apparatus and methods are provided to detect whether a device is in contact with skin and to determine the pigmentation level of skin. To determine skin contact, the apparatus and methods utilize light emitted onto the skin and detectors and sensors to measure spectral remission from the skin. The apparatus and methods further compare the obtained remission measurement with known skin spectral remission values. The sensors may be calibrated to allow measurements of absolute remission to be converted to fractional remission values. Measurements of skin pigmentation levels are compared to known base-line levels to determine appropriate treatment parameters.

The apparatus and methods may be used by incorporating the apparatus into the device itself, such as into a light based dermatologic or cosmetic treatment device, or the apparatus may be remote from and remotely control the treatment device.

The apparatus includes one or more light sources and one or more detectors. The one or more light sources may be a single broad band source or multiple single spectrum sources. The one or more detectors may be a single broad band detector or multiple detectors each sensitive to a unique optical band. In one embodiment, a single broad band source is utilized together with multiple detectors. In a second embodiment, multiple single spectrum sources are utilized together with a single broad band detector. In a third embodiment, multiple single spectrum sources are utilized together with multiple detectors each sensitive to a unique optical band.

The apparatus and methods of the present invention include use of measured and calculated values to control operation of the device, for instance, to allow the device to turn on or to prevent the device from turning on, or, alternatively, to adjust emission levels of the device to correspond to the treatment appropriate with the measured and calculated values.

In alternative embodiments of the present invention, the apparatus and methods include temperature sensors that compensate for temperature fluctuations.

In one embodiment of the present invention, the device is incorporated within a dermatological treatment device which is self-contained, hand-held, and battery powered. A skin sensor in this embodiment compensates for temperature fluctuations and inhibits emission of the treatment device unless the presence of skin is detected and further inhibits emission unless the pigmentation level of the skin is less than a predetermined threshold level. In an alternative embodiment, the emission level is adjustable in accordance with the determined pigmentation level of the skin.

Figure 1:
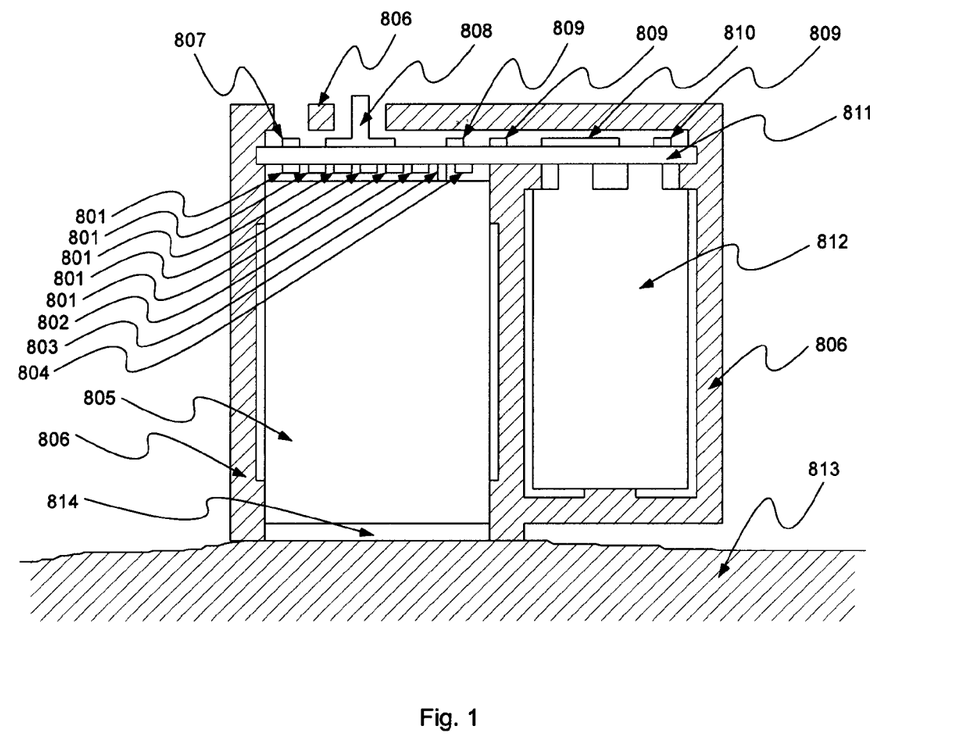
FIG. 1 illustrates in cross-sectional view an embodiment of the optical portion of a device in accordance with the invention.
Figure 2:
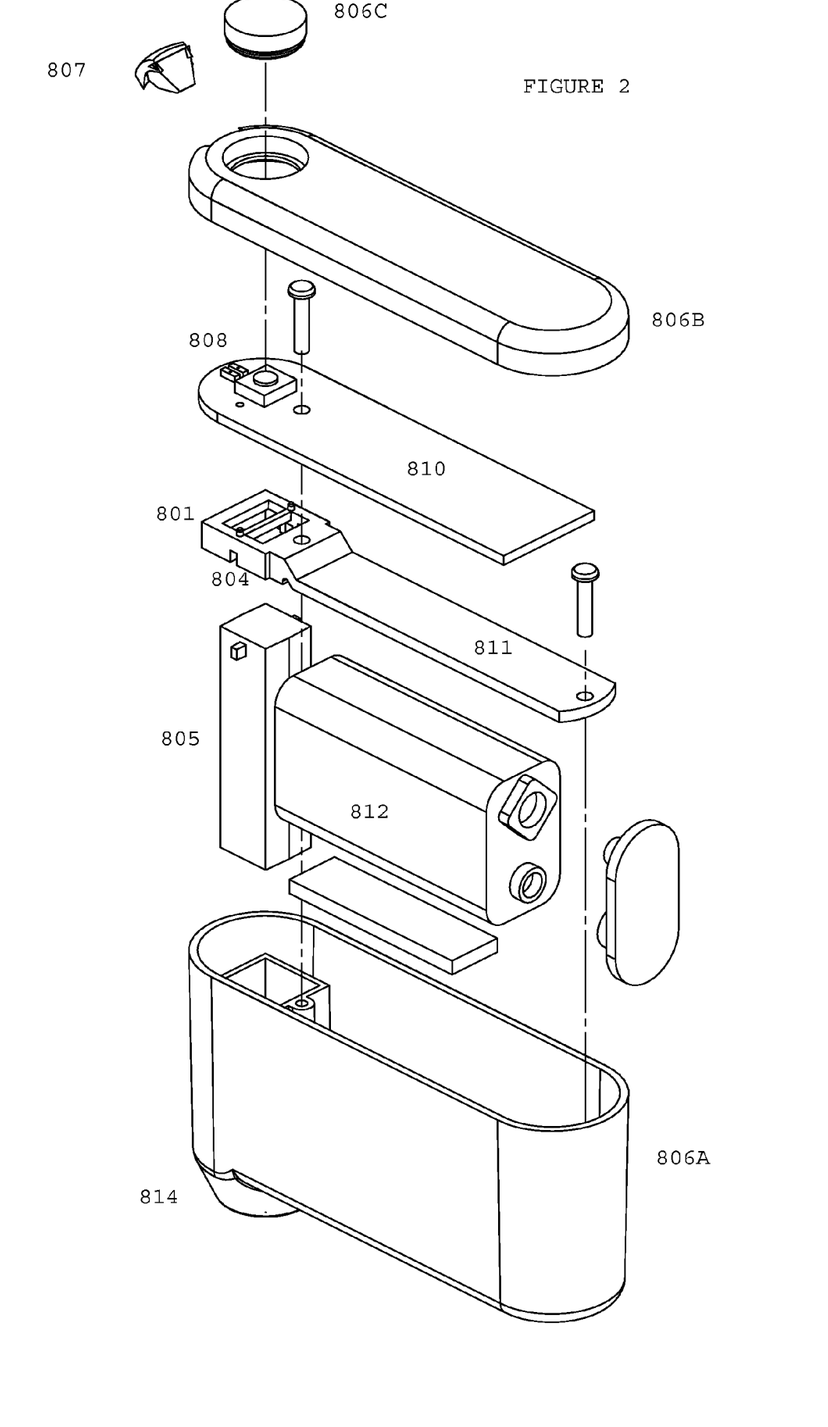
FIG. 2 illustrates in exploded isometric view the major components of a device as shown in FIG. 1.
Figure 3:
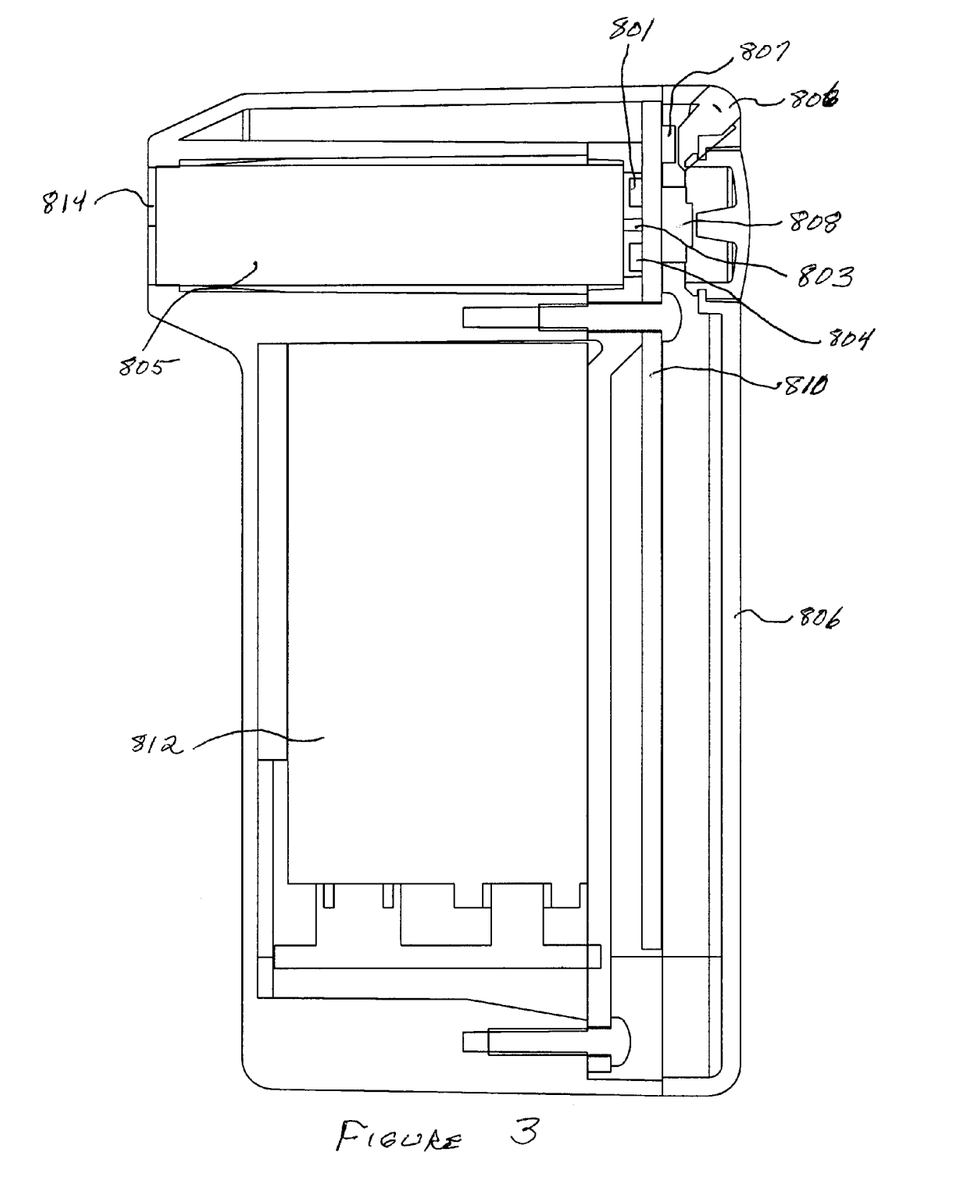
FIG. 3 illustrates in cross-sectional side a device as shown in FIG. 2.

Referring now to FIGS. 1-3, an embodiment of the present invention is shown in various views. In the illustrated embodiment, the present invention is contained within a housing 806A-B which, depending upon the implementation, can be either a housing separate from a treatment device or the housing of the treatment device itself. When used, a measurement aperture 814 is held against the surface of skin 813 or any other material that is suitably flat over the area of the measurement aperture. The user turns on the electronics by pressing switch 808, or any other suitable arrangement, to begin the measurement. The switch 808 is actuated by pressing button 806C. Contained within housing 806A-B are light sources 801 which emit light into a lightguide, or mixer 805. Each of light sources 801 emits a distinct and unique wavelength band, such as LED's operating in, for example, blue, green, yellow, red and infrared bands, as shown in Table I, below:

| LED colors used in Skin Sensor | Peak Emission Wavelength(nm) | Spectral Line Half-Width(nm) |
| --- | --- | --- |
| LED GREEN | 574 | 15 |
| LED SUPER RED | 639 | 20 |
| LED YELLOW | 588 | 15 |
| LED BLUE | 468 | 25 |
| LED INFRARED(IR) | 940 | 50 |

Mixer 805 is an optically transparent material made from acrylic plastic, quartz, sapphire, glass or other suitable material for transporting light having a proximal surface nearest the sources 801 and distal surface furthest from sources 801. The walls of mixer 805 are sufficiently smooth to reduce scattering of light and to ensure that substantially all the light incident on the side walls undergoes total internal reflection. In some embodiments, mixer 805 is comprised of a material whose index of refraction is greater than about 1.5. This ensures that substantially all of the light from sources 801 that is incident on the proximal surface of mixer 805 that is not reflected by the proximal surface of mixer 805 will undergo total internal reflection when incident on the side walls of mixer 805. In some alternative embodiments, a hollow light guide can be used. In an embodiment, the length and width of mixer 805 are chosen so that the light transported by mixer 805 is substantially spatially uniform when incident on the distal surface of mixer 805. In some embodiments, a baffle 803, is incorporated into the skin sensor so that light that undergoes Fresnel reflection when incident on the proximal surface of mixer 805 is not reflected into detector 804, since the intensity of that light would not be remitted from the skin or other surface being tested.

Light entering the proximal end of mixer 805 will travel the length of the mixer 805 to the distal end where substantially all of the light leaves the mixer and exits the device through measurement aperture 814.

In some embodiments, some of the light incident on the distal end of mixer 805 can be reflected back towards detector 804 and could contribute a non-significant offset in the measurement. To overcome this, during calibration a measurement into a black surface is made so that the light reflected by this black surface can be measured and then subtracted from subsequent measurements.

In some embodiments, a significant amount of the light that is remitted by the skin may not be collected, and therefore measured, by the device of the present invention. This is because the light incident upon the skin from the device can scatter laterally in the skin, and remit outside the area covered by the aperture of the device. The extent to which such lateral scattering occurs in skin varies with wavelength, where the scattering of blue light is small compared with the scattering of red and infrared light. In materials other than skin, the extent of such scattering can be greater or less depending upon the properties of those materials. However, such lateral scattering in skin is compensated for in at least some embodiments because the scattering adds a reproducible offset to the measurements. The lateral scattering effect can therefore be adjusted for when comparing the sample to the "known spectral remittance of skin". This compensation can be used, depending upon the embodiment, both when determining whether the sampled material is skin and also when comparing the sampled material against threshold value(s) for determining pigmentation level.

Light exiting the measurement aperture 814 of the device is incident on the skin 813 or other surface held against the measurement aperture 814 of the device. Light incident on the skin 813 or other surface is either reflected back into the mixer or enters the skin 813 or other surface. Once inside the material being measured, the light undergoes scattering and absorption. A portion of the light entering the skin is remitted by the skin 813 or other material being measured and travels back towards the detector 804 at the proximal end of the mixer. In one embodiment, the detector 804 is a broadband detector, although detector 804 can be replaced in other embodiments by a plurality of detectors, each matched to the wavelength of one the light sources 801.

In use, each of the sources 801 is turned on sequentially, in turn, and a measurement is made of the intensity of the light remitted by the skin for that source 801 by detector 804.

In some embodiments, a temperature sensor 802 is located sufficiently near sources 801 and detector 804 so that the temperature of the sources 801 and detector 804 can be measured at nearly the same time as the remission measurement. The temperature sensor 802 can be a thermistor, thermocouple, or other suitable means for sensing the temperature in the vicinity of the sources 801 and detector 804.

In one embodiment, the device comprises a printed circuit board (PCB) 811 on which the sources 801, detector 804, temperature sensor 802, and a switch 808 are mounted. Also mounted on the PCB 811 are a processor 810, battery 812, and other electronics components 809 suitable for powering the light sources 801, and for interfacing with the temperature sensor 802, detector 804, switch 808, and indicator 807.

Processor 810 can be a simple 8 bit microcontroller. Common microcontrollers are capable of storing calibration constants and can compute the fraction of light that is remitted, including computing the fraction of light remitted for each light source. Using appropriate programming, once the spectral remission has been calculated, the processor determines whether the spectral remission is within the range indicative of skin. Additionally the processor is programmed to determine the level of pigmentation. One suitable algorithm for determining skin pigmentation is to measure the amount of light remitted at the red wavelength and compare this to a predefined threshold. The predetermined red threshold can vary significantly depending upon the implementation, but in at least some embodiments is set in the range of 20%-40%, before adjusting for the lateral scattering effect discussed above. In some embodiments, the red threshold is set at 28% or lower, while in other embodiments the red threshold is set to 34% or higher. If a scattering loss of approximately 30% is assumed, a 28% threshold setting becomes a 40% real threshold, 28%/(1−0.3)=40%.

Other algorithms can be used, for example algorithms considering additional wavelengths, or algorithms including adjustments for temperature or noise. The red wavelength has been determined to offer advantages over other wavelengths because it has comparatively high remission, and is less affected by variations in temperature. Alternatively, an LED operating at the same wavelength as the treatment device, for example 810 nm, can be used.

Whichever algorithm is programmed into the processor 810, the processor determines (1) whether the spectral remission is suitably similar to skin, and (2) whether the pigmentation is below that which would present a hazard to the user undergoing treatment. The result is displayed by indicator 807. The display 807 can be a simple "go/no go" display or, alternatively, can display the results of both the skin test, i.e., skin or not skin, and the pigmentation level.

Depending upon the results of the various tests, the present invention can communicate with the treatment device to either permit or prevent emissions from the treatment device. Alternatively, the maximum fluence permitted to be emitted by the treatment device can be adjusted in accordance with the pigmentation level determined by the device of the present invention. If the device of the present invention is integrated into the treatment device, such adjustment can be implemented into the processor used to control emissions. If the device of the present invention is separate from the treatment device, the two can communicate by any suitable means, such as a wired or wireless link. Wireless links include infrared, RF, and so on, and can use any suitable protocol.

In some embodiments, the processor 810 is also programmed to correct for temperature variations at the sources 801 and detector 804. In an embodiment, the correction factor for each temperature is stored in a lookup table. Alternatively, the temperature correction factor can be implemented algorithmically. In some embodiments, temperature compensation is provided both for LED power and phototransistor sensitivity, and the LED's and phototransistor can have opposite sensitivities so that the net sensitivity can be either positive or negative depending on whether the LED sensitivity dominates the detector sensitivity, or viceversa. Depending on the wavelength, both positive and negative adjustments can be applied. In an embodiment, the correction is linear with temperatures over the temperature range that the detection device is expected to operate.

Figure 4:
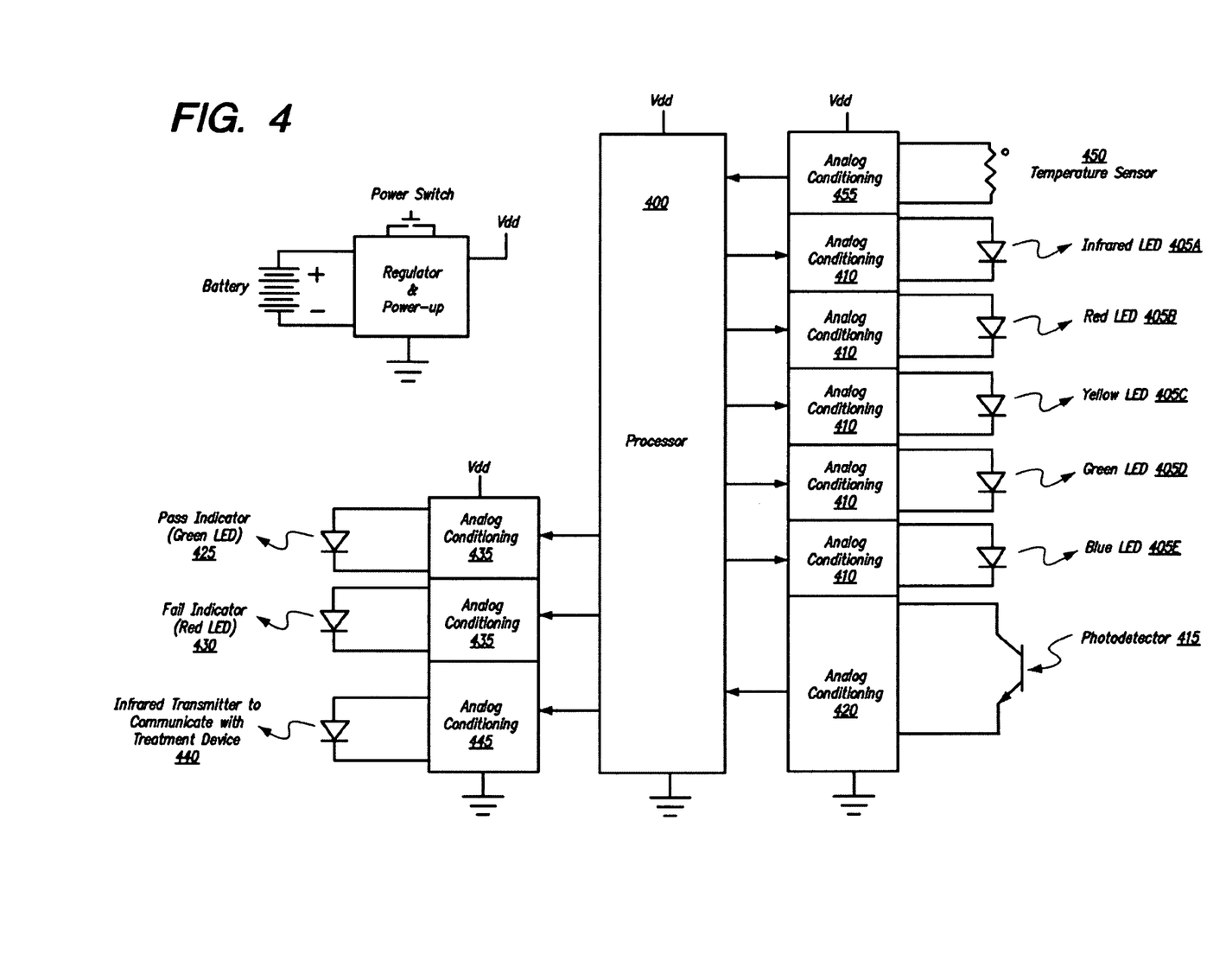
FIG. 4 illustrates a schematic diagram of the circuit of an embodiment of the invention.

FIG. 4 illustrates in schematic diagram of the circuit of an embodiment of the invention, in which a processor 400 sequentially pulses LEDs 405A-405E, each of which is a different wavelength band, with appropriate signal conditioning 410. The LED's illuminate the material being testing, generally skin, and the remittance from the skin for each wavelength is detected by photodetector 415, which sends the information to the processor after appropriate signal conditioning 420. The processor then determines whether the material being tested is skin, using the algorithms discussed above, and also determines the level of pigmentation as discussed above. Depending upon the result, one of indicators 425 or 430 is energized by the processor through appropriate signal conditioning 435. The indicators can, depending upon the embodiment, simply be a red or green LED, or can be an alphanumeric display. If the present invention is not integrated into the treatment device, the processor can also communicate with the treatment device using, for example, an infrared transmitter 440 after appropriate signal conditioning 445. A temperature sensor 450 also provides an input to the processor 400 to permit the processor to compensate for temperature-induced performance variations in the LEDs and photodetector.

In the event that the device determines that the skin being tested is too heavily pigmented for safe use of the maximum fluence available from the associated treatment device, the present invention includes inhibiting the emissions of the treatment device. Such inhibition can take the form of preventing emissions above a predetermined threshold, or can proportionately degrade the fluence of one or more output levels normally available from the treatment device. For example, if a treatment device offers three fluence levels, but the pigmentation is too high for safe operation at the two top levels, in some embodiments the top two levels are simply inhibited. In other embodiments, the top two, or even all three, levels can be proportionately diminished, or shifted, to ensure safe operation. In still other embodiments, particularly for devices where the detection device and treatment device are integrated, the pigmentation is tested before each emission, and the fluence is adjusted to be appropriate for that level of pigmentation, or at least not to exceed a safe threshold for that level of pigmentation.

As stated above, the optical sensor apparatus may be integrated into various dermatologic and cosmetic devices. For purposes of illustration only, and without limited the scope of the present invention, the device may be integrated into the dermatologic devices shown in U.S. Pat. Nos. 7,452,356, 7,250,045, and 7,118,563, which are hereby incorporated by reference in their entirety. The optical sensor apparatus is incorporated into these devices by placing the sensors/detectors around the output window of the device. Alternatively, optical fibers may be used to deliver light from the sensors to the area of the output window when the optical sensors are mounted behind the output window. In another embodiment, remission light is returned to the detectors through the mixer.

Having fully described a preferred embodiment of the invention and various alternatives, those skilled in the art will recognize, given the teachings herein, that numerous alternatives and equivalents exist which do not depart from the invention. It is therefore intended that the invention not be limited by the foregoing description, but only by the appended claims.

What is claimed is:

1. A dermatological treatment system, comprising:
   an optical device for analyzing a target surface, the optical device comprising:
      a housing having a surface contacting portion;
      one or more light sources provided in the housing and configured to emit light toward a target surface proximate the surface contacting portion;
      one or more detectors provided in the housing and configured to detect remitted light from the target surface at one or more different wavelengths;
      control circuitry coupled to the one or more light sources and the one or more detectors, the control circuitry comprising:
         a processor; and
         computer instructions stored in non-transitory computer-readable media and programmed to:
            perform a remittance analysis including analyzing the detected remittance at the one or more different wavelengths to determine at least one of (a) whether the target surface is skin or (b) a pigmentation of the target surface; and
      a wireless transmitter coupled to the control circuitry, wherein the wireless transmitter wirelessly transmits results of the remittance analysis;
   a treatment radiation source configured to emit treatment radiation toward a user;
   a wireless receiver that receives the results of the remittance analysis transmitted by the wireless transmitter of the optical device; and
   a controller configured to control radiation emission by the treatment radiation source based on the results of the remittance analysis received via the wireless receiver.

2. The dermatological treatment system of claim 1 further composing a temperature sensor coupled to the control circuitry.

3. The dermatological treatment system of claim 1 wherein the one or more light sources comprises a single broad band light source, and the one or more detectors comprises a single broad band detector.

4. The dermatological treatment system of claim 1 wherein the one or more light sources comprises multiple light sources, each of the multiple light sources emitting light at a different wavelength, and the one or more detectors comprises a single broad band detector.

5. The dermatological treatment system claim 1 wherein the one or more light sources comprises multiple light sources, each of the multiple light sources emitting light at a different wavelength, and the one or more detectors comprises multiple detectors, each of the multiple detectors detecting a different wavelength.

6. The dermatological treatment system of claim 1 wherein the one or more light sources comprises one or more LEDs selected from green, red, super red, yellow, blue and infrared LEDs.

7. The dermatological treatment system of claim 1 further comprising an indicator coupled to the control circuitry.

8. The dermatological treatment system of claim 7 wherein the indicator provides an indication to a user based on the remitted light detected by the one or more detectors.

9. A dermatologic treatment device comprising:
   a housing;
   a treatment radiation source within the housing capable of being activated to emit treatment radiation toward a user;
   an optical control system mounted within the housing, the optical control system comprising:
      one or more light sources configured to emit light toward a target surface;
      a first detector configured to detect remitted light from the target surface at a first wavelength; and
      control circuitry including a processor and computer instructions stored in a computer-readable medium and programmed to:
         determine both (a) whether the target surface is skin and (b) the pigmentation of the target surface using the detected remittance at the first wavelength as detected by the first detector, and
         control radiation emission by the treatment radiation source of the dermatologic treatment device based on (a) the determination of whether the target surface is skin and (b) the determined pigmentation of the target surface,
      wherein the computer instructions are programmed with:
         a first algorithm that determines whether the target surface is skin based on the detected remittance at multiple different wavelengths, including the detected remittance at the first wavelength as detected by the first detector, and
         a second algorithm that determines the pigmentation of the target surface based on the detected remittance a subset of the multiple different wavelengths, the subset including the detected remittance at the first wavelength as detected by the first detector, such that detected remittance at the first wavelength as detected by the first detector is used for both the determination of whether the target surface is skin and the determination of the pigmentation of the target surface.

10. The dermatologic treatment device of claim 9 wherein the optical control system further comprises a temperature sensor coupled to the control circuitry.

11. The dermatologic treatment device of claim 9 wherein the one or more light sources comprises a single broad band light source, and the optical control system includes the first detector and at least one further detector.

12. The dermatologic treatment device of claim 9 wherein the one or more light sources comprises multiple light sources, each of the multiple light sources emitting light at a different wavelength, and the first detector comprises a single broad band detector.

13. The dermatologic treatment device of claim 9 wherein the one or more light sources comprises multiple light sources, each of the multiple light sources emitting light at a different wavelength, and the optical control system includes multiple detectors, including the first detector and at least one further detector, each of the multiple detectors detecting a different wavelength.

14. The dermatologic treatment device of claim 9 wherein the one or more light sources comprise one or more LEDs selected from green, red, super red, yellow, blue and infrared LEDs.

15. The dermatologic treatment device of claim 9 further comprising an indicator coupled to the control circuitry.

16. The dermatologic treatment device of claim 15 wherein the indicator provides an indication to a user based on the remitted light detected by the one or more detectors.

17. The optical device of claim 1 wherein the one or more light sources comprises a single broad band light source, and the one or more detectors comprises multiple detectors, each configured to detect a different optical band.

18. A method for analyzing a target surface using an optical device, the method comprising:
operating an optical device comprising:
a housing having a surface contacting portion;
one or more light sources provided in the housing and configured to emit light toward a target surface proximate the surface contacting portion;
a first detector provided in the housing and configured to detect remitted light from the target surface at a first wavelength; and
control circuitry coupled to the one or more light sources and the first detector; and
determining, by the control circuitry, whether the target surface is skin based on the detected remittance at the multiple different wavelengths, including the detected remittance at the first wavelength as detected by the first detector, and
determining, by the control circuitry, a pigmentation of the target surface based on the detected remittance at a subset of the multiple different wavelengths, the subset including the detected remittance at the first wavelength as detected by the first detector,
such that such that the detected remittance at the first wavelength as detected by the first detector is used for determining both (a) whether the target surface is skin and (b) the pigmentation of the target surface, and
controlling, by the control circuitry, at least one aspect of radiation emission by a dermatologic treatment source of a dermatologic treatment device based on (a) the determination of whether the target surface is skin and (b) the determined pigmentation of the target surface.

19. The method of claim 18, wherein the subset of the multiple different wavelengths is a single wavelength.

20. The optical device of claim 1, wherein controlling radiation emission by the treatment radiation source based on the results of the remittance analysis comprises preventing radiation emission by the treatment radiation source based on the results of the remittance analysis.

21. The optical device of claim 1, wherein controlling radiation emission by the treatment radiation source based on the results of the remittance analysis comprises controlling an emission level emitted by the treatment radiation source based on the results of the remittance analysis.

22. The method of claim 18, wherein the optical control system includes multiple detectors including the first detector and at least one further detector, wherein each of the multiple detectors is configured to detect a different wavelength.

23. The method of claim 18, wherein the first detector comprises a broad band detector.

* * * * *